United States Patent [19]

Eicken et al.

[11] Patent Number: 6,143,745
[45] Date of Patent: Nov. 7, 2000

[54] PROCESS AND AGENT FOR CONTROLLING HARMFUL FUNGI

[75] Inventors: Karl Eicken, Wachenheim; Eberhard Ammermann, Heppenheim; Siegfried Strathmann, Limburgerhof; Gisela Lorenz, Hambach; Harald Köhle, Bobenheim; Günter Retzlaff, Römerberg, all of Germany

[73] Assignee: BASF Aktiengesellschaft, Ludwigshafen, Germany

[21] Appl. No.: 09/171,524

[22] PCT Filed: Apr. 22, 1997

[86] PCT No.: PCT/EP97/02037

§ 371 Date: Oct. 21, 1998

§ 102(e) Date: Oct. 21, 1998

[87] PCT Pub. No.: WO97/39630

PCT Pub. Date: Oct. 30, 1997

[30] Foreign Application Priority Data

Apr. 22, 1996 [DE] Germany ............... 196 15 976

[51] Int. Cl.⁷ .................. A01N 43/40; A01N 43/56; A01N 43/58
[52] U.S. Cl. .................. 514/247; 514/355; 514/406; 514/407
[58] Field of Search .................. 514/247, 355, 514/406, 407

[56] References Cited

U.S. PATENT DOCUMENTS

| 4,843,068 | 6/1989 | Hamaguchi et al. ............. 514/63 |
| 5,438,070 | 8/1995 | Eicken et al. ............. 514/403 |

FOREIGN PATENT DOCUMENTS

| 134439 | 3/1985 | European Pat. Off. . |
| 256503 | 2/1988 | European Pat. Off. . |
| 289879 | 11/1988 | European Pat. Off. . |
| 545099 | 6/1993 | European Pat. Off. . |
| 61145106 | 12/1984 | Japan . |
| 04077402 | 7/1990 | Japan . |
| 04235104 | 1/1991 | Japan . |
| 93/11117 | 6/1993 | WIPO . |
| 97/08952 | 3/1997 | WIPO . |

OTHER PUBLICATIONS

Colby, *Weeds*, 15, 1967, pp. 20–22.

*Primary Examiner*—Allen J. Robinson
*Attorney, Agent, or Firm*—Keil & Weinkauf

[57] ABSTRACT

Compositions for controlling harmful fungi, containing in a solid or liquid carrier pyridaben of the formula:

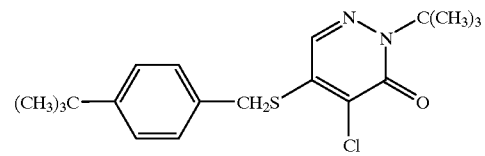

or fenpyroximate of the formula:

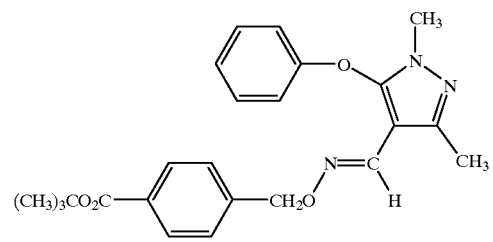

or tebufenpyrad of the formula:

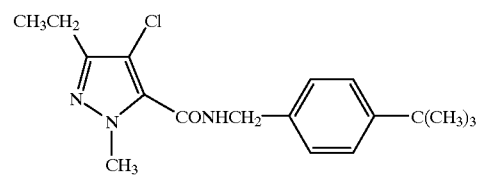

and at least one amide compound of the following formula I:

$$A\text{—}CO\text{—}NR^1R^2 \qquad (I)$$

where the substituents have the meanings indicated in the description, and methods for controlling harmful fungi using compositions of this type are described.

15 Claims, No Drawings

PROCESS AND AGENT FOR CONTROLLING HARMFUL FUNGI

This application is a 371 of PCT/EP97/02037, filed Apr. 22, 1997.

The present invention relates to compositions for controlling harmful fungi and methods for controlling harmful fungi using compositions of this type.

EP-A-545 099 describes anilide compounds of the formula

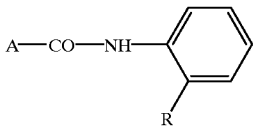

where A is phenyl which is substituted in the 2-position by methyl, trifluoromethyl, chlorine, bromine or iodine or is certain aromatic or nonaromatic heterocyclic radicals, which can be unsubstituted or substituted by methyl, chlorine or trifluoromethyl, and R is certain aliphatic or cycloaliphatic radicals, which can be unsubstituted or substituted by halogen, or is phenyl which is unsubstituted or substituted by $C_1$–$C_4$-alkyl, $C_1$–$C_4$-alkoxy, $C_1$–$C_4$-alkylthio or halogen. These compounds can be used for controlling Botrytis.

EP-A-589 301 describes anilide compounds of the same formula, where A is a cyclic radical of the formula:

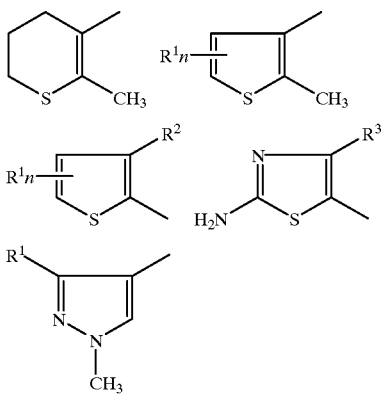

where $R^1$ is hydrogen or $C_1$–$C_4$-alkyl; $R^2$ is halogen or $C_1$–$C_4$-alkyl; $R^3$ is $C_1$–$C_4$-alkyl or $C_1$–$C_4$-haloalkyl; n is 1 or 2; and R essentially has the meanings indicated above. These compounds can also be used for treating Botrytis.

WO 93/11117 describes compounds of the formula

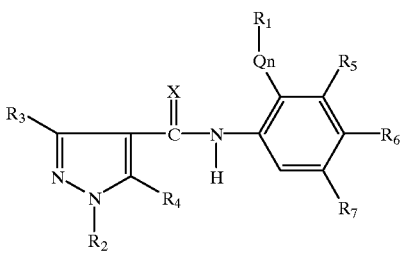

where
Q is $C_{1-3}$-alkyl, $C_2$–$C_3$-alkenyl, $C_2$–$C_3$-alkynyl, —($CH_2$)$_m$CH= or —($CH2$)$_m$—X—($CH_2$)$_m$—;
n is 0 or 1;
each m independently of one another is 0, 1, 2 or 3;
each X independently is O or S;
$R^1$ is certain alicyclic radicals;
$R^2$ is hydrogen, fluorinated methyl, methyl, ethyl, $C_2$–$C_6$-alkenyl, $C_3$–$C_6$-chloroalkyl, phenyl, alkylthioalkyl, alkoxyalkyl, haloalkylthioalkyl, haloalkoxyalkyl or hydroxyalkyl;
$R^3$ is halomethyl, halomethoxy, methyl, ethyl, halogen, cyano, methylthio, nitro, aminocarbonyl or aminocarbonylmethyl;
$R^4$ is hydrogen, halogen or methyl;
$R^5$, $R^6$ and $R^7$ are each independently of one another selected from hydrogen, halogen, cyano, $C_1$–$C_6$-alkyl, $C_2$–$C_6$-alkenyl, $C_2$–$C_6$-alkynyl, $C_{1-4}$-alkoxy, $C_{1-4}$-alkylthio, $C_3$–$C_4$-cycloalkyl and halomethoxy. These compounds are fungicidally active.

It is an object of the present invention to make available an improved possibility of controlling harmful fungi and in particular Botrytis.

Surprisingly, we have found that this object is achieved by a composition which as active compounds contains the substances pyridaben (CAS Reg. No. 96489-71-3), fenpyroximate (CAS Reg. No. 111812-58-9) or tebufenpyrad (CAS Reg. No. 119168-77-3) (The Pesticide Manual, 10th edition, 1994) known as acaricides and amide compounds of the following formula I.

The invention therefore relates to compositions for controlling harmful fungi, which, in a solid or liquid carrier, contain pyridaben of the formula:

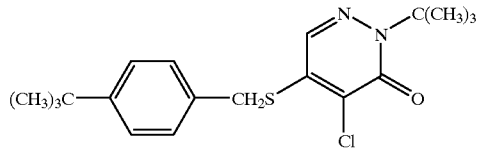

or fenpyroximate of the formula:

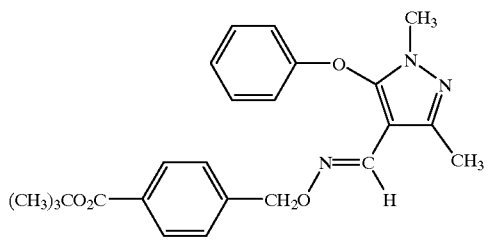

or tebufenpyrad of the formula:

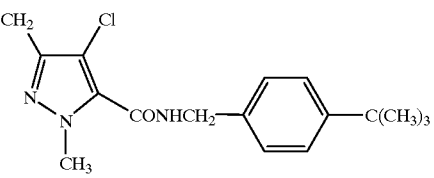

and at least one amide compound of the following formula I:

(I)

where
- A is an aryl group or an aromatic or nonaromatic, 5- or 6-membered heterocycle which has 1 to 3 heteroatoms which are selected from O, N and S;

it being possible for the aryl group or the heterocycle, if appropriate, to have 1, 2 or 3 substituents which independently of one another are selected from alkyl, halogen, $CHF_2$, $CF_3$, alkoxy, haloalkoxy, alkylthio, alkylsulfynyl and alkylsulfonyl;

- $R^1$ is a hydrogen atom;
- $R^2$ is a phenyl or cycloalkyl group which, if appropriate, has 1 2 or 3 substituents which are selected from alkyl, alkenyl, alkynyl, alkoxy, alkenyloxy, alkynyloxy, cycloalkyl, cycloalkenyl, cycloalkyloxy, cycloalkenyloxy, phenyl and halogen, it being possible for the aliphatic and cycloaliphatic radicals to be partially or completely halogenated and/or for the cycloaliphatic radicals to be substituted by 1 to 3 alkyl groups and for the phenyl group to have 1 to 5 halogen atoms and/or 1 to 3 substituents which independently of one another are selected from alkyl, haloalkyl, alkoxy, haloalkoxy, alkylthio and haloalkylthio, and it being possible for the amide phenyl group to be fused to a saturated, 5-membered ring which is unsubstituted or substituted by one or more alkyl groups and/or can have a heteroatom selected from O and S.

The abovementioned compositions can contain the acaricides individually or in any combination.

The compositions according to the invention have a synergistic action and are therefore particularly suitable for controlling harmful fungi and in particular Botrytis.

In the context of the present invention halogen is fluorine, chlorine, bromine or iodine and in particular fluorine, chlorine or bromine.

The term "alkyl" includes straight-chain and branched alkyl groups. In this case, they are preferably straight-chain or branched $C_1$–$C_{12}$-alkyl groups and in particular $C_{1-6}$-alkyl groups. Examples of alkyl groups are alkyl such as, in particular, methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1, 3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group defined as above, which is partially or completely halogenated by one or more halogen atoms, in particular fluorine or chlorine. Preferably, 1 to 3 halogen atoms are present, the difluoromethane or the trifluoromethyl group being particularly preferred.

The above remarks regarding the alkyl group and haloalkyl group correspondingly apply to the alkyl and haloalkyl groups in alkoxy, haloalkoxy, alkylthio, haloalkylthio, alkylsulfynyl and alkylsulfonyl.

The alkenyl group includes straight-chain and branched alkenyl groups. In this case, they are preferably straight-chain or branched $C_3$–$C_{12}$-alkenyl groups and in particular $C_3$–$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group can be partially or completely halogenated by one or more halogen atoms, in particular fluorine and chlorine. Preferably, it has 1 to 3 halogen atoms.

The alkynyl group includes straight-chain and branched alkynyl groups. In this case, they are preferably straight-chain or branched $C_3$–$C_{12}$-alkynyl groups and in particular $C_3$–$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-l-methyl-2-propynyl.

The above details regarding the alkenyl group and its halogen substituents and regarding the alkynyl group correspondingly apply to alkenyloxy and alkynyloxy.

The cycloalkyl group is preferably a $C_3$–$C_6$-cycloalkyl group, such as cyclopropyl, cyclobutyl, cyclopentyl or cyclohexyl. If the cycloalkyl group is substituted, it preferably has 1 to 3 $C_1$–$C_4$-alkyl radicals as substituents.

Cycloalkenyl is preferably a $C_4$–$C_6$-cycloalkenyl group, such as cyclobutenyl, cyclopentenyl or cyclohexenyl. If the cycloalkenyl group is substituted, it preferably has 1 to 3 $C_1$–$C_4$-alkyl radicals as substituents.

A cycloalkoxy group is preferably a $C_5$–$C_6$-cycloalkoxy group, such as cyclopentyloxy or cyclohexyloxy. If the cycloalkoxy group is substituted, it preferably has 1 to 3 $C_1$–$C_4$-alkyl radicals as substituents.

The cycloalkenyloxy group is preferably a $C_{5\text{-}}C_6$-cycloalkenyloxy group, such as cyclopentenyloxy or cyclohexenyloxy. If the cycloalkenyloxy group is substituted, it preferably has 1 to 3 $C_1$–$C_4$-alkyl radicals as substituents.

Aryl is preferably phenyl.

If A is a phenyl group, this can have one, two or three of the abovementioned substituents in any desired position. Preferably, these substituents are selected independently of one another from alkyl, difluoromethyl, trifluoromethyl and halogen, in particular chlorine, bromine and iodine. Particularly preferably, the phenyl group has one substituent in the 2-position.

If A is a 5-membered heterocycle, it is particularly a furyl, thiazolyl, pyrazolyl, imidazolyl, oxazolyl, thienyl, triazolyl or thiadiazolyl radical or the corresponding dihydro or tetrahydro derivatives thereof. A thiazolyl or pyrazolyl radical is preferred.

If A is a 6-membered heterocycle, in this case it is particularly a pyridyl radical or a radical of the formula:

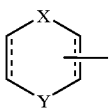

where one of the radicals X and Y is O, S or $NR^9$, $R^9$ being H or alkyl and the other of the radicals X and Y being $CH_2$, S, SO, $SO_2$ or $NR^9$. The dashed line means that, if appropriate, a double bond can be present.

Particularly preferably, the 6-membered aromatic heterocycle is a pyridyl radical, in particular a 3-pyridyl radical, or a radical of the formula

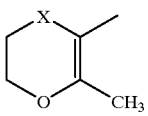

(A3)

where X is $CH_2$, S, SO or $SO_2$.

The heterocyclic radicals mentioned can, if appropriate, have 1, 2 or 3 of the abovementioned substituents, these substituents preferably being selected independently of one another from alkyl, halogen, difluoromethyl or trifluoromethyl.

Particularly preferably, A is a radical of the formula:

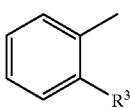

(A1)

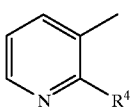

(A2)

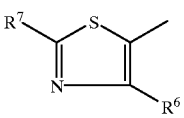

(A5)

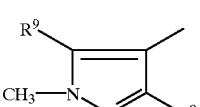

(A7)

where $R^3$, $R^4$, $R^6$, $R^7$, $R^8$ and $R^9$ independently of one another are hydrogen, alkyl, in particular methyl, halogen, in particular chlorine, $CHF_2$ or $CF_3$.

The radical $R^1$ in the formula I is preferably a hydrogen atom.

The radical $R^2$ in the formula I is preferably a phenyl radical. Preferably, $R^2$ has at least one substituent which is particularly preferably in the 2-position. Preferably, the substituent (or the substituents) is (are) selected from alkyl, cycloalkyl, cycloalkenyl, halogen or phenyl.

The substituents of the radical $R^2$, for their part, can in turn be substituted. The aliphatic or cycloaliphatic substituents can in this case be partially or completely halogenated, in particular fluorinated or chlorinated. Preferably, they have 1, 2 or 3 fluorine or chlorine atoms. If the substituent of the radical $R^2$ is a phenyl group, this can preferably be substituted by 1 to 3 halogen atoms, in particular chlorine atoms, and/or by a radical which is preferably selected from alkyl and alkoxy. The phenyl group is particularly preferably substituted by a halogen atom in the p-position, ie. the particularly preferred substituent of the radical $R^2$ is a p-halosubstituted phenyl radical. The radical $R^2$ can also be fused to a saturated 5-membered ring, it being possible for this ring for its part to have 1 to 3 alkyl substituents.

$R^2$ is then, for example, indanyl, thiaindanyl or oxaindanyl. Indanyl or 2-oxaindanyl, which, in particular, are bonded to the nitrogen atom via the 4-position, are preferred.

According to a preferred embodiment, the composition according to the invention contains as amide compound a compound of the formula I, where A has the following meanings:

phenyl, pyridyl, dihydropyranyl, dihydrooxathiinyl, dihydrooxathiinyl oxide, dihydrooxathiinyl dioxide, furyl, thiazolyl, pyrazolyl or oxazolyl, it being possible for these groups to have 1, 2 or 3 substituents which independently of one another are selected from alkyl, halogen, difluoromethyl and trifluoromethyl.

According to a further preferred embodiment A is:

pyridin-3-yl, which is unsubstituted or substituted in the 2-position by halogen, methyl, difluoromethyl, trifluoromethyl, methoxy, methylthio, methylsulfynyl or methylsulfonyl;

phenyl which is unsubstituted or substituted in the 2-position by methyl, trifluoromethyl, chlorine, bromine or iodine;

2-methyl-5,6-dihydropyran-3-yl;

2-methyl-5,6-dihydro-1,4-oxathiin-3-yl or the 4-oxide or 4,4-dioxide thereof;

2-methylfuran-3-yl, which is unsubstituted or substituted in the 4- and/or 5-position by methyl;

thiazol-5-yl, which is unsubstituted or substituted in the 2-and/or 4-position by methyl, chlorine, difluoromethyl or trifluoromethyl;

thiazol-4-yl, which is unsubstituted or substituted in the 2-and/or 5-position by methyl, chlorine, difluoromethyl or trifluoromethyl;

1-methylpyrazol-4-yl, which is unsubstituted or substituted in the 3- and/or 5-position by methyl, chlorine, difluoromethyl or trifluoromethyl; or oxazol-5-yl, which is unsubstituted or substituted in the 2-and/or 4-position by methyl or chlorine.

According to a further preferred embodiment, the compositions according to the invention contain as amide compound a compound of the formula I, where $R^2$ is a phenyl group which is unsubstituted or substituted by 1, 2 or 3 of the abovementioned substituents.

According to a further preferred embodiment, the compositions according to the invention contain as amide compound a compound of the formula I, where $R^2$ is a phenyl group which in the 2-position has one of the following substituents:

$C_3$–$C_6$-alkyl, $C_5$–$C_6$-cycloalkenyl, $C_5$–$C_6$-cycloalkyloxy, cycloalkenyloxy, it being possible for these groups to be substituted by 1, 2 or 3 $C_1$–$C_4$-alkyl groups, phenyl, which is substituted by 1 to 5 halogen atoms and/or 1 to 3 groups which independently of one another are selected from $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, indanyl or oxaindanyl, which is unsubstituted or substituted by 1, 2 or 3 $C_1$–$C_4$-alkyl groups.

According to a further preferred embodiment, the compositions according to the invention contain as amide compound a compound of the formula Ia,

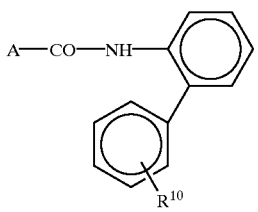 (Ia)

where

A is

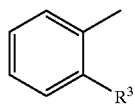 (A1)

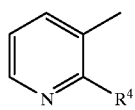 (A2)

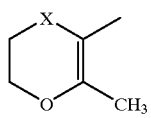 (A3)

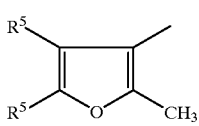 (A4)

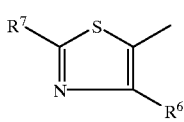 (A5)

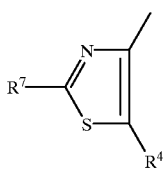 (A6)

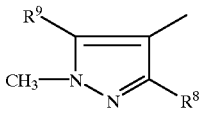 (A7)

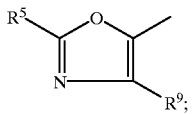 (A8)

X is methylene, sulfur, sulfynyl or sulfonyl ($SO_2$),
$R^3$ is methyl, difluoromethyl, trifluoromethyl, chlorine, bromine 30 or iodine,
$R^4$ is trifluoromethyl or chlorine,
$R^5$ is hydrogen or methyl,
$R^6$ is methyl, difluoromethyl, trifluoromethyl or chlorine,
$R^7$ is hydrogen, methyl or chlorine,
$R^8$ is methyl, difluoromethyl or trifluoromethyl,
$R^9$ is hydrogen, methyl, difluoromethyl, trifluoromethyl or chlorine,
$R^{10}$ is $C_1$–$C_4$-alkyl, $C_1$–$C_4$-alkoxy, $C_1$–$C_4$-alkylthio or halogen.

According to a particularly preferred embodiment, the compositions contain as amide compound a compound of the formula Ib

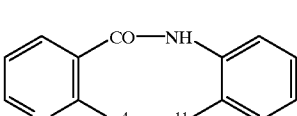 (Ib)

where
$R^4$ is halogen and
$R^{11}$ is phenyl which is substituted by halogen.

Amide compounds which can be used are mentioned in EP-A-545 099 and 589 301, to which reference is entirely made hereby.

The preparation of the amide compounds of the formula I is disclosed, for example, in EP-A-545 099 or 589 301 or can be carried out by similar processes.

In order to display synergistic action, even a small amount of amide compound of the formula I is sufficient. Pyridaben, fenpyroximate or tebufenpyrad and the amide compound are preferably employed in a weight ratio which is in the range from 20:1 to 1:20, in particular 10:1 to 1:10.

The invention also relates to a method of controlling harmful fungi, which comprises treating the fungi, their habitat or the materials, plants, seeds, soils, surfaces or spaces to be protected from fungal attack with a composition according to the invention, it being possible for the active compounds pyridaben, fenpyroximate or tebufenpyrad and the amide compound to be applied simultaneously, to be precise together or separately, or in succession.

The compositions according to the invention can be applied by spraying, atomizing, dusting, broadcasting or watering, for example in the form of directly sprayable solutions, powders, suspensions, even high-percentage aqueous, oily or other suspensions, or dispersions, emulsions, oil dispersions, pastes, dusting compositions, broadcasting compositions or granules. The application forms depend on the intended uses; they should in any case guarantee the finest possible distribution of the active compounds according to the invention.

Normally, the plants are sprayed or dusted with the active compounds or the seeds of the plants are treated with the active compounds.

The formulations are prepared in a known manner, e.g. by extending the active compound using solvents and/or carriers, if desired using emulsifiers and dispersants, it being possible if water is used as a diluent also to use other organic solvents as auxiliary solvents. Suitable auxiliaries for this are in the main: solvents such as aromatics (e.g. xylene), chlorinated aromatics (e.g. chlorobenzenes), paraffins (e.g. petroleum fractions), alcohols (e.g. methanol, butanol), ketones (e.g. cyclohexanone), amines (e.g. ethanolamine, dimethylformamide) and water; carriers such as ground natural minerals (e.g. kaolins, aluminas, talc, chalk) and ground synthetic minerals (e.g. highly disperse silicic acid, silicates); emulsifiers such as nonionic and anionic emulsifiers (e.g. polyoxyethylene fatty alcohol ethers, alkylsulfonates and arylsulfonates) and dispersants such as lignin-sulfite waste liquors and methylcellulose.

Suitable surface-active substances are the alkali metal, alkaline earth metal and ammonium salts of aromatic sulfonic acids, e.g. lignosulfonic, phenolsulfonic, naphthalenesulfonic and dibutylnaphthalenesulfonic acid, and also of fatty acids, alkyl-and alkylarylsulfonates, alkyl, lauryl ether and fatty alcohol sulfates, as well as salts of sulfated hexa-, hepta- and octadecanols, and also fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ethers, ethoxylated isooctyl-, octyl- or nonylphenol, alkylphenyl or tributylphenyl polyglycol ethers, alkylaryl polyether alcohols, isotridecyl alcohol, fatty alcohol-ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, e.g. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground synthetic materials, fertilizers, such as ammonium sulfate, ammonium phosphate, ammonium nitrate, ureas and vegetable products, such as cereal flour, tree bark, wood and nutshell meal, cellulose powder or other solid carriers.

Examples of such preparations which contain the active compounds pyridaben, fenpyroximate or tebufenpyrad and the amide compound in a weight ratio of 8:1 are:

I. a solution of 90 parts by weight of the active compounds and 10 parts by weight of N-methylpyrrolidone, which is suitable for application in the form of very small drops;

II. a mixture of 20 parts by weight of the active compounds, 80 parts by weight of xylene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of castor oil; by finely dispersing the solution in water a dispersion is obtained;

III. an aqueous dispersion of 20 parts by weight of the active compounds, 40 parts by weight of cyclohexanone, 30 parts by weight of isobutanol, 20 parts by weight of the addition product of 40 mol of ethylene oxide to 1 mol of castor oil;

IV. an aqueous dispersion of 20 parts by weight of the active compounds, 25 parts by weight of cyclohexanol, 65 parts by weight of a mineral oil fraction of boiling point 210 to 280° C. and 10 parts by weight of the addition product of 40 mol of ethylene oxide to 1 mol of castor oil;

V. a mixture, ground in a hammer mill, of 80 parts by weight of the active compounds, 3 parts by weight of the sodium salt of diisobutylnaphthalene-1-sulfonic acid, 10 parts by weight of the sodium salt of a lignosulfonic acid from a sulfite waste liquor and 7 parts by weight of powdered silica gel; by finely dispersing the mixture in water a spray mixture is obtained;

VI. an intimate mixture of 3 parts by weight of the active compounds and 97 parts by weight of finely divided kaolin; this dusting composition contains 3% by weight of active compound;

VII. an intimate mixture of 30 parts by weight of the active compounds, 92 parts by weight of powdered silica gel and 8 parts by weight of paraffin oil, which has been sprayed onto the surface of this silica gel; this preparation gives the active compounds a good adherence;

VIII. a stable aqueous dispersion of 40 parts by weight of the active compounds, 10 parts by weight of the sodium salt of a phenolsulfonic acid-urea-formaldehyde condensate, 2 parts by weight of silica gel and 48 parts by weight of water, which can be further diluted;

IX. a stable oily dispersion of 20 parts by weight of the active compounds, 2 parts by weight of the calcium salt of dodecylbenzenesulfonic acid, 8 parts by weight of fatty alcohol polyglycol ether, 20 parts by weight of the sodium salt of a phenolsulfonic acid-urea-formaldehyde condensate and 88 parts by weight of a paraffinic mineral oil.

The compositions according to the invention are distinguished by an outstanding activity against a broad spectrum of phytopathogenic fungi, in particular against Botrytis. In some cases they are systemically active (ie. they can be absorbed by the treated plant without loss of action and, if appropriate, transported in the plant) and can be employed as foliar and soil fungicides.

They are of particular importance for the control of a multiplicity of fungi on various crop plants such as wheat, rye, barley, oats, rice, corn, grass, cotton, soybeans, coffee, sugar cane, vines, fruit and decorative plants and vegetable plants such as cucumbers, beans and cucurbits, and on the seeds of these plants.

The compositions are applied by treating the fungi or the seeds, plants, materials or the soil to be protected from fungal attack with a fungicidally active amount of the active compounds.

Application is carried out before or after the infection of the materials, plants or seeds by the fungi.

The compositions are especially suitable for controlling the following plant diseases:

*Erysiphe graminis* (powdery mildew) in cereals,
*Erysiphe cichoracearum* and *Sphaerotheca fuliginea* on cucurbits,
*Podosphaera leucotricha* on apples,
*Uncinula necator* on vines,
*Venturia inaequalis* (scab) on apples,
Helminthosporium species on cereals,
*Septoria nodorum* on wheat,
*Botrytis cinerea* (grey mold) on strawberries, vines,
*Cercospora arachidicola* on groundnuts,
*Pseudocercosporella herpotrichoides* on wheat, barley,
*Pyricularia oryzae* on rice,
Fusarium and Verticillium species on various plants,
Alternaria species on vegetables and fruit,
Monilinia species in fruit,
Sclerotinia species in rape and vegetables.

Application against Botrytis is preferred.

The compositions can also be employed in material protection (wood preservation), eg. against *Paecilomyces variotii*.

The fungicidal compositions in general contain from 0.1 to 95, preferably from 0.5 to 90, % by weight of active compound.

The application rates, depending on the effect desired, are from 0.02 to 3 kg of active compound per ha.

In the treatment of seed, in general amounts of active compound of from 0.001 to 50 g, preferably 0.01 to 10 g, are needed per kilogram of seed.

In the application form as fungicides, the compositions according to the invention can also contain other active compounds, eg. herbicides, insecticides, growth regulators, fungicides or alternatively fertilizers.

On mixing with fungicides, in many cases an increase in the fungicidal spectrum of action is obtained here.

The following list of fungicides with which the compounds according to the invention can be applied together is intended to illustrate the combination possibilities, but not to restrict them:

sulfur,
dithiocarbonates and their derivatives, such as ferric dimethyldithiocarbamate,
zinc dimethyldithiocarbamate,
zinc ethylenebisdithiocarbamate,
manganese ethylenebisdithiocarbamate,
manganese zinc ethylenediamine-bis-dithiocarbamate,
tetramethylthiuram disulfide,
ammonia complex of zinc (N,N-ethylene-bis-dithiocarbamate),
ammonia complex of zinc (N,N'-propylene-bis-dithiocarbamate),
zinc (N,N'-propylene-bis-dithiocarbamate),
N,N'-polypropylene-bis(thiocarbamoyl) disulfide,
nitro derivatives, such as dinitro(1-methylheptyl)phenyl crotonate,
2-sec-butyl-4,6-dinitrophenyl 3,3-dimethylacrylate,
2-sec-butyl-4,6-dinitrophenyl isopropyl carbonate,
diisopropyl 5-nitroisophthalate;
heterocyclic substances, such as
2-heptadecyl-2-imidazoline acetate,
2,4-dichloro-6-(o-chloroanilino)-s-triazine,
o,o-diethyl phthalimidophosphonothioate,
5-amino-1-β-[bis (dimethylamino)phosphinyl]-3-phenyl-1,2,4-triazole,
2,3-dicyano-1,4-dithioanthraquinone,
2-thio-1,3-dithiolo-β-[4,5-b]quinoxaline,
methyl 1-(butylcarbamoyl)-2-benzimidazole carbamate,
2-methoxycarbonylaminobenzimidazole,
2-(fur-2-yl)benzimidazole,
2-(thiazol-4-yl)benzimidazole,
N-(1,1,2,2-tetrachloroethylthio)tetrahydrophthalimide,
N-trichloromethylthiotetrahydrophthalimide,
N-trichloromethylthiophthalimide,
N-dichlorofluoromethylthio-N',N'-dimethyl-N-phenylsulfamide,
5-ethoxy-3-trichloromethyl-1,2,3-thiadiazole,
2-thiocyanatomethylbenzothiazole,
1,4-dichloro-2,5-dimethoxybenzene,
4-(2-chlorophenylhydrazono)-3-methyl-5-isoxazolone,
5 2-thiopyridine-1-oxide,
8-hydroxyquinoline or its copper salt,
2,3-dihydro-5-carboxanilido-6-methyl-1,4-oxathiin,
2,3-dihydro-5-carboxanilido-6-methyl-1,4-oxathiin-4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethylfuran-3-carboxylic acid cyclohexylamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethyl acetate,
piperazine-1,4-diylbis(1-(2,2,2-trichloroethyl))formamide,
1-(3,4-dichloroanilino)-1-formylamino-2,2,2-trichloroethane,
2,6-dimethyl-N-tridecylmorpholine or its salts,
2,6-dimethyl-N-cyclododecylmorpholine or its salts,
N-[3-(p-tert-butylphenyl)-2-methylpropyl]-cis-2,6-dimethylmorpholine,
N-[3-(p-tert-butylphenyl)-2-methylpropyl]piperidine,
1-[2-(2,4-dichlorophenyl)-4-ethyl-1,3-dioxolan-2-ylethyl]-1H-1,2,4-triazole
1-[2-(2,4-dichlorophenyl)-4-n-propyl-1,3-dioxolan-2-ylethyl]-1H-1,2,4-triazole
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)-2-butanone,
1-(4-chlorophenyl)-3,3-dimethyl-1-(1H-1,2,4-triazol-1-yl)-2-butanol,
α-2-chlorophenyl)-α-( 4-chlorophenyl)-5-pyrimidinemethanol,
5-butyl-2-dimethylamino-4-hydroxy-6-methylpyrimidine,
bis(p-chlorophenyl)-3-pyridinemethanol,
1,2-bis(3-ethoxycarbonyl-2-thioureido)benzene,
1,2-bis(3-methoxycarbonyl-2-thioureido)benzene,
and various fungicides, such as
dodecylguanidine acetate,
3-[3-(3,5-dimethyl)-2-oxycyclohexyl-2-hydroxyethyl] glutarimide, hexachlorobenzene,
DL-methyl-N-(2,6-dimethylphenyl)-N-2-furoyl alaninate,
DL-N-(2,6-dimethylphenyl)-N-(2'-methoxyacetyl) alanine methyl ester
N-(2,6-dimethylphenyl)-N-chloroacetyl-D,L-2-aminobutyrolactone,
DL-N-(2,6-dimethylphenyl)-N-(phenylacetyl)alanine methyl ester,
5-methyl-5-vinyl-3-(3,5-dichlorophenyl)-2,4-dioxo-1,3-oxazolidine,
3-(3,5-dichlorophenyl)-5-methyl-5-methoxymethyl-1,3-oxazolidine-2,4-dione,
3-(3,5-dichlorophenyl)-1-isopropylcarbamoylhydantoin,
N-(3,5-dichlorophenyl)-1,2-dimethylcyclopropane-1,2-dicarboximide,
2-cyano-[N-ethylaminocarbonyl-2-methoximino]acetamide
1-[2-(2,4-dichlorophenyl)pentyl]-1H-1,2,4-triazole,
2,4-difluoro-α-(1H-1,2,4-triazol-1-ylmethyl)benzhydryl alcohol,
N-(3-chloro-2,6-dinitro-4-trifluoromethylphenyl)-5-trifluoromethyl-3-chloro-2-aminopyridine,
1-(bis(4-fluorophenyl)methylsilyl)methyl-1H-1,2,4-triazole,
[2-(4-chlorophenyl)ethyl]-(1,1-dimethylethyl)-1H-1,2,4-triazole-1-ethanol, 1-[3-(2-chlorophenyl)-1-(4-fluorophenyl)oxiran-2-ylmethyl]-1H-1,2,4-triazole,
strobilurins such as methyl E-methoximino-[α-(o-tolyloxy)-o-tolyl]acetate, methyl E-2-{2-[6-(2-cyanophenoxy) pyrimidin-4-yloxy]phenyl}-3-methoxyacrylate, methyl E-methoximino-[α-(2,5-dimethyloxy)-o-tolyl]acetamide,
anilinopyrimidines such as N-(4,6-dimethylpyrimidin-2-yl) aniline,
N-[4-methyl-6-(1-propynyl)pyrimidin-2-yl]aniline,
N-(4-methyl-6-cyclopropylpyrimidin-2-yl)aniline,
phenylpyrroles such as 4-(2,2-difluoro-1,3-benzodioxol-4-yl)-pyrrole-3-carbonitrile,
cinnamides such as 3-(4-chlorophenyl)-3-(3,4-dimethoxyphenyl)-acrylic acid morpholide.

The synergistic action of the compositions according to the invention is illustrated with the aid of the following use examples:

The amide compounds used were the compounds I.1 and I.2 of the formulae

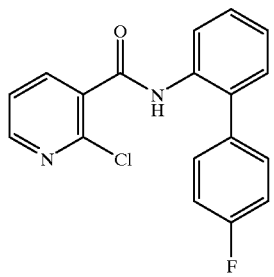

I.1

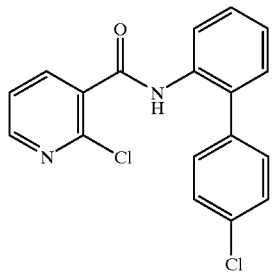

I.2

Use Example 1

Activity Against Botrytis cinerea

Paprika seedlings of the variety "Neusiedler Ideal Elite" were sprayed until dripping wet, after 4 to 5 leaves had developed well, with aqueous suspensions, which contained 80% of active compound and 20% of emulsifier in the dry matter. After the spray coating had dried on, the plants were sprayed with a conidia suspension of the fungus Botrytis cinerea and placed in a chamber with high atmospheric humidity at 22–24° C. After 5 days, the disease had developed on the untreated control plants so severely that the resulting leaf necroses covered the greater part of the leaves (attack 83%).

The visually determined values for the percentage proportion of affected leaf area were converted into efficiencies as % of the untreated control. Efficiency 0 is equal to attack as in the untreated control, efficiency 100 is 0% attack. The efficiencies to be expected for active compound combinations were determined by the Colby formula (Colby, S. R. "Calculating synergistic and antagonistic responses of herbicide combinations", Weeds, 15 , pp. 20 to 22 (1967) and compared with the observed efficiencies. The results are indicated in Table 1 which follows.

TABLE 1

| | Active compound concentration in ppm | | Efficiency in % of the control | |
|---|---|---|---|---|
| Active compound | Tebufenpyrad | Active compound I.1 or I.2 | observed | calculated *) |
| control (untreated) | — | — | 0 | |
| Tebufenpyrad | 250 | — | 0 | |
| I.1 | — | 16 | 3 | |
| I.2 | — | 16 | 64 | |
| | — | 8 | 52 | |
| Tebufenpyrad + I.1 | 250 | 16 | 28 | 3 |
| Tebufenpyrad + I.2 | 250 | 16 | 82 | 64 |
| | 250 | 8 | 88 | 52 |

*) calculated according to the Colby formula

From the results of the test, it emerges that the observed efficiency in all mixing ratios is higher than the efficiency precalculated according to the Colby formula, i.e. a synergistic effect is present.

Use Example 2

Activity Against Botrytis cinerea on Peppers

Slices of green peppers were sprayed with an aqueous active compound preparation which contained 80% of active compound and 20% of emulsifier in the dry matter until dripping wet. 2 hours after the spray coating had dried on, the fruit slices were inoculated with a spore suspension of Botrytis cinerea, which contained $1.7 \times 10^6$ spores per ml of a 2% strength biomalt solution. The inoculated fruit slices were then incubated in humid chambers at 18° C. for 4 days. The development of Botrytis on the attacked fruit slices was then assessed visually (100% attack). The amide compound used was the above compound ±2.

The visually determined values for the percentage proportion of attacked leaf area were converted into efficiencies as % of the untreated control. Efficiency 0 is equal to attack as in the untreated control, efficiency 100 is 0% attack. The efficiencies to be expected for active compound combinations were determined by the Colby formula (Colby, S. R. "Calculating synergistic and antagonistic responses of herbicide combinations", Weeds, 15, pp. 20 to 22, 1967) and compared with the observed efficiencies. The results are indicated in Table 2 which follows.

TABLE 2

| Active compound | Active compound concentration in ppm | | Efficiency in % of the control | |
|---|---|---|---|---|
| | Tebufenpyrad | Active compound I.2 | observed | calculated *) |
| control (untreated) | — | — | 0 | |
| Tebufenpyrad | 250 | — | 15 | |
| I.2 | — | 31 | 36 | |
| Tebufenpyrad + I.2 | 250 | 31 | 58 | 46 |

*) calculated according to the Colby formula

From the results of the test, it emerges that the observed efficiency in all mixing ratios is higher than the efficiency precalculated according to the Colby formula, i.e. a synergistic effect is present.

What is claimed is:

1. A composition for controlling harmful fungi, comprising a solid or liquid carrier and synergistically effective amounts of an acaricide selected from the group consisting of: pyridaben of the formula

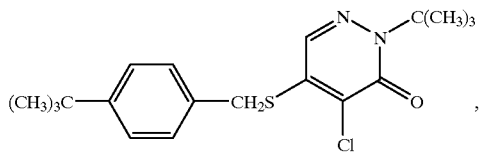

fenpyroximate of the formula

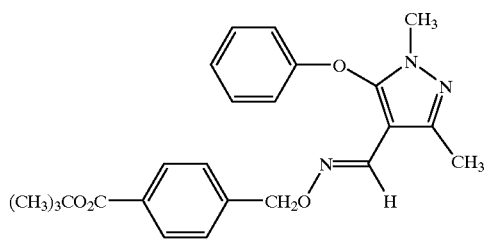

and tebufenpyrad of the formula

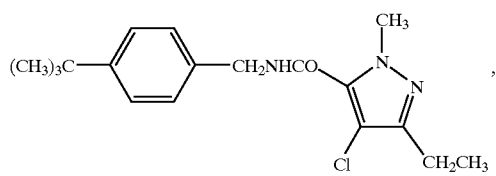

and at least one amide compound of the formula I:

A—CO—NR¹R²     (I)

wherein
A is pyridyl which is unsubstituted or substituted by 1, 2 or 3 substituents selected from the group consisting of alkyl, halogen, $CHF_2$ and $CF_3$;
$R^1$ is a hydrogen atom;
$R^2$ is a phenyl or cycloalkyl group which is unsubstituted or substituted by 1, 2 or 3 substituents which independently of one another are selected from alkyl, alkenyl, alkynyl, alkoxy, alkenyloxy, alkynyloxy, cycloalkyl, cycloalkenyl, cycloalkoxy, cycloalkenyloxy, phenyl and halogen, wherein the aliphatic and cycloaliphatic radicals are unsubstituted or may be partially or completely halogenated and the cycloaliphatic radicals may further be substituted by 1 to 3 alkyl groups, and wherein the phenyl group is unsubstituted or substituted by 1 to 5 halogen atoms and may further be substituted by 1 to 3 substituents which independently from one another are selected from alkyl, haloalkyl, alkoxy, haloalkoxy, alkylthio and haloalkylthio, and wherein the phenyl group may further be fused to a saturated, 5-membered ring which is unsubstituted or substituted by one or more alkyl groups and/or can have a hetero atom selected from O and S.

2. The composition defined in claim 1, wherein A is pyridin-3-yl which is unsubstituted or substituted in the 2-position by halogen, methyl, difluoromethyl or trifluoromethyl.

3. The composition defined in claim 1, wherein

A is pyridin-3-yl which is unsubstituted or carries 1, 2 or 3 substituents selected from the group consisting of alkyl, halogen, $CHF_2$ and $CF_3$, and $R^2$ is phenyl which is unsubstituted or carries 1, 2 or 3 substituents selected from the group consisting of alkyl, alkenyl, alkynyl, alkoxy, alkenyloxy, alkynyloxy, cycloalkyl, cycloalkenyl, cycloalkoxy, cycloalkenyloxy, phenyl and halogen, wherein the aliphatic and cycloaliphatic radicals are unsubstututed or partially or fully halogenated, and wherein the cycloaliphatic radicals are unsubstituted or substituted by 1 to 3 alkyl groups, and wherein the phenyl group is unsubstituted or substituted by 1 to 5 halogen atoms and/or 1 to 3 substituents selected from the group consisting of alkyl, haloalkyl, alkoxy, haloalkoxy, alkylthio and haloalkylthio, or wherein the phenyl group is fused to a saturated 5-membered ring which is unsubstituted or substituted by one or more alkyl groups and/or can have, as a ring member, a hetero atom selected from the group consisting of O and S.

4. The composition defined in claim 1, wherein $R^2$ is phenyl which carries one of the following substituents in the 2-position: alkyl, cycloalkyl, cycloalkenyl, halogen or phenyl, wherein the phenyl group is unsubstituted or substituted by 1 to 3 halogen atoms, an alkyl or an alkoxy radical, or is fused to a saturated 5-membered ring which is unsubstituted or substituted by 1 to 3 alkyl groups.

5. The composition defined in claim 1, wherein the amide compound is of the formula Ia

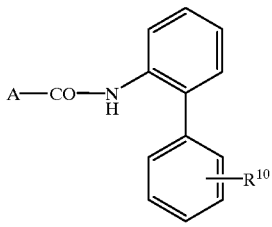

wherein A is a pyridyl group of formula A2,

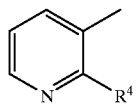

wherein $R^4$ is trifluoromethyl or chlorine $R^{10}$ is $C_1$–$C_4$-alkyl, $C_1$–$C_4$-alkoxy, $C_1$–$C_4$-alkylthio or halogen.

6. The composition defined in claim 1, wherein the amide compound is of the formula Ib

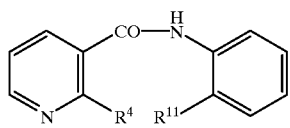

wherein $R^4$ is halogen and $R^{11}$ is phenyl which is substituted by halogen.

7. The composition defined in claim 1, wherein the amide compound is of the formula

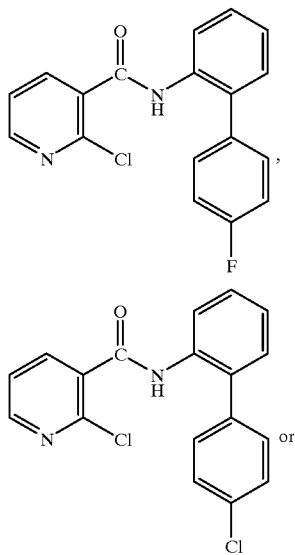

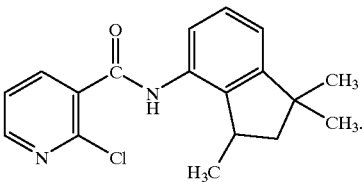

8. The composition defined in claim 1, which is formulated in two parts, one part containing the acaricide in a solid or liquid carrier and the other part containing the amide compound in a solid or liquid carrier.

9. A method for controlling harmful fungi, which comprises treating the fungi, their habitat or materials, plants, seeds, soils, surfaces or spaces which are to be protected from fungal attack with a fungicidally effective amount of the composition defined in claim 1, it being possible for the effective amounts of the acaricide and the amide compound to be applied simultaneously or in succession.

10. The method of claim 9, wherein A is pyridin-3-yl which is unsubstituted or substituted in the 2-position by halogen, methyl, difluoromethyl or trifluoromethyl.

11. The method of claim 9, wherein

A is pyridin-3-yl which is unsubstituted or carries 1, 2 or 3 substituents selected from the group consisting of alkyl, halogen, $CHF_2$ and $CF_3$, and $R^2$ is phenyl which is unsubstituted or carries 1, 2 or 3 substituents selected from the group consisting of alkyl, alkenyl, alkynyl, alkoxy, alkenyloxy, alkynyloxy, cycloalkyl, cycloalkenyl, cycloalkoxy, cycloalkenyloxy, phenyl and halogen, wherein the aliphatic and cycloaliphatic radicals are unsubstututed or partially or fully halogenated, and wherein the cycloaliphatic radicals are unsubstituted or substituted by 1 to 3 alkyl groups, and wherein the phenyl group is unsubstituted or substituted by 1 to 5 halogen atoms and/or 1 to 3 substituents selected from the group consisting of alkyl, haloalkyl, alkoxy, haloalkoxy, alkylthio and haloalkylthio, or wherein the phenyl group is fused to a saturated 5-membered ring which is unsubstituted or substituted by one or more alkyl groups and/or can have, as a ring member, a hetero atom selected from the group consisting of O and S.

12. The method of claim 9, wherein $R^2$ is phenyl which carries one of the following substituents in the 2-position: alkyl, cycloalkyl, cycloalkenyl, halogen or phenyl, wherein the phenyl group is unsubstituted or substituted by 1 to 3 halogen atoms, an alkyl or an alkoxy radical, or is fused to a saturated 5-membered ring which is unsubstituted or substituted by 1 to 3 alkyl groups.

13. The method of claim 9, wherein the amide compound is of the formula Ia

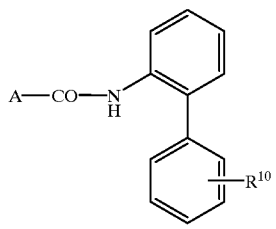
wherein A is a pyridyl group of formula A2
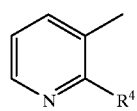
wherein $R^4$ is trifluoromethyl or chlorine $R_{10}$ is $C_1$–$C_4$-alkyl, $C_1$–$C_4$-alkoxy, $C_1$–$C_4$-alkylthio or halogen.
14. The method of claim 9, wherein the amide compound is of the formula Ib
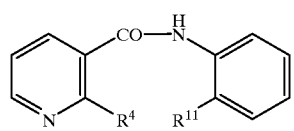
wherein $R^4$ is halogen and $R^{11}$ is phenyl which is substituted by halogen.
15. The method of claim 9, wherein the amide compound is of the formula
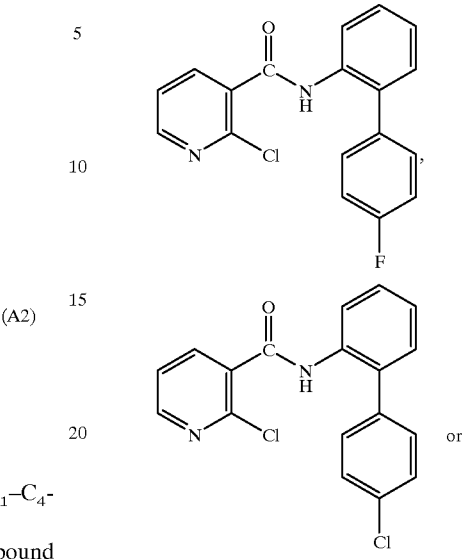
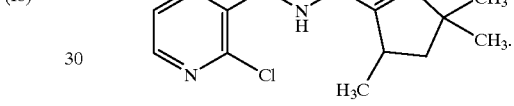
* * * * *

UNITED STATES PATENT AND TRADEMARK OFFICE
CERTIFICATE OF CORRECTION

PATENT NO.: 6,143,745

DATED: November 7, 2000

INVENTOR(S): EICKEN et al.

It is certified that error appears in the above-identified patent and that said Letters Patent is hereby corrected as shown below:

Col. 1, line 48, "$C_{1-4}$-" should be --$C_1$-$C_4$--- (3 occurrences).

Col. 2, line 15, "$C_{1-4}$-" should be --$C_1$-$C_4$--- (2 occurrences).

Col. 3, line 12, "1 2 or 3" should be --1, 2 or 3--.

Col. 3, line 37, "$C_{1-6}$-" should be --$C_1$-$C_6$- --.

Col. 4, line 28, "4-alkynyl" should be --4-hexynyl--.

Col. 4, line 51, "$C_5$-$C_6$-" should be --$C_5$-$C_6$- --.

Col. 7, line 67, delete "30".

Col. 11, line 35, "o,o-diethyl" should be --O,O-diethyl--.

Col. 11, line 50, "2-thiocyanatomethylbenzothiazole," should be --2-thiocyanatomethylbenzothiazole,--.

UNITED STATES PATENT AND TRADEMARK OFFICE
CERTIFICATE OF CORRECTION

PATENT NO. : 6,143,745
DATED : November 7, 2000
INVENTOR(S) : EICKEN et al.

It is certified that error appears in the above-identified patent and that said Letters Patent is hereby corrected as shown below:

Col. 16, claim 3, line 44, "unsubstututed" should be --unsubstituted--.

Col. 18, claim 11, line 44, "unsubstututed" should be --unsubstituted--.

Col. 19, claim 13, line 23, "$R_{10}$" should be --$R^{10}$--.

Signed and Sealed this

First Day of May, 2001

Attest:

NICHOLAS P. GODICI

*Attesting Officer*     *Acting Director of the United States Patent and Trademark Office*